(12) United States Patent
Feldhahn et al.

(10) Patent No.: US 12,138,392 B2
(45) Date of Patent: *Nov. 12, 2024

(54) DEVICE FOR POSITIONING A PATIENT INTERFACE

(71) Applicant: Loewenstein Medical Technology S.A., Luxembourg (LU)

(72) Inventors: Karl-Andreas Feldhahn, Hamburg (DE); Arnold Frerichs, Buxtehude (DE); Martin Bechtel, Winsen/Luhe (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 364 days.

This patent is subject to a terminal disclaimer.

(21) Appl. No.: 17/452,102

(22) Filed: Oct. 25, 2021

(65) Prior Publication Data

US 2022/0054785 A1    Feb. 24, 2022

Related U.S. Application Data

(63) Continuation of application No. 16/192,895, filed on Nov. 16, 2018, now Pat. No. 11,160,946, which is a
(Continued)

(30) Foreign Application Priority Data

Nov. 15, 2012    (DE) .......................... 102012022355.2

(51) Int. Cl.
| | |
|---|---|
| *A61M 16/06* | (2006.01) |
| *A61M 16/08* | (2006.01) |
| *F16F 1/377* | (2006.01) |

(52) U.S. Cl.
CPC ........ *A61M 16/0655* (2014.02); *A61M 16/06* (2013.01); *A61M 16/0644* (2014.02);
(Continued)

(58) Field of Classification Search
CPC .......... A61M 16/0633; A61M 16/0638; A61M 16/0644; A61M 16/065; A61M 16/0655;
(Continued)

(56) References Cited

U.S. PATENT DOCUMENTS

| | | |
|---|---|---|
| 3,792,702 A | 2/1974 | Delest |
| 5,868,384 A | 2/1999 | Anderson |
(Continued)

FOREIGN PATENT DOCUMENTS

| | | |
|---|---|---|
| DE | 202013100755 U1 | 3/2013 |
| EP | 2005985 A2 | 12/2008 |
(Continued)

OTHER PUBLICATIONS

Lee Spring, "Stock Springs & Custom Springs", 2011 Catalog, retrieved from https://web.archive.org/web/20111019225959/http://leespring.com/downloads/catalog/2011/2011LeeSpringCatalog.pdf (Year: 2011).

*Primary Examiner* — Joseph D. Boecker
(74) *Attorney, Agent, or Firm* — Abel Schillinger, LLP

(57) ABSTRACT

Disclosed is a spring element which is suitable for use with a patient interface and in the form of an elongated body and has an axis along which the spring element is compressed. Arranged in a direction of the axis, the spring element comprises a first region and a second region, at least one characteristic of the spring element in the first region having a value which is different from a value of the at least one characteristic in the second region.

10 Claims, 17 Drawing Sheets

Related U.S. Application Data continuation of application No. 14/078,748, filed on Nov. 13, 2013, now Pat. No. 10,137,272.

(52) U.S. Cl.
CPC ......... *A61M 16/0683* (2013.01); *F16F 1/377* (2013.01); *A61M 16/0825* (2014.02)

(58) Field of Classification Search
CPC .......... F16F 1/043; F16F 1/047; F16F 1/3665; F16F 2224/005; B21F 35/00; B21F 35/003; B21F 35/006
See application file for complete search history.

(56) References Cited

U.S. PATENT DOCUMENTS

| | | | |
|---|---|---|---|
| 6,612,556 B2 | 9/2003 | Petrina | |
| 7,971,590 B2 | 7/2011 | Frater et al. | |
| 8,176,916 B2 | 5/2012 | Chang | |
| 8,544,470 B2 | 10/2013 | Chien | |
| 8,720,443 B2 | 5/2014 | Kooij et al. | |
| 10,137,272 B2 * | 11/2018 | Feldhahn | F16F 1/377 |
| 10,737,048 B2 | 8/2020 | Frerichs | |
| 11,160,946 B2 * | 11/2021 | Feldhahn | A61M 16/06 |
| 2004/0112387 A1 | 6/2004 | Lang | |
| 2004/0158930 A1 * | 8/2004 | Gladney | A47C 23/0438 5/256 |
| 2006/0118117 A1 | 6/2006 | Berthon-Jones et al. | |
| 2007/0215161 A1 * | 9/2007 | Frater | A61M 16/065 128/206.24 |
| 2008/0053446 A1 | 3/2008 | Sleeper | |
| 2008/0314388 A1 | 12/2008 | Brambilla et al. | |
| 2008/0314390 A1 * | 12/2008 | Kwok | A61M 16/0638 128/207.11 |
| 2009/0095301 A1 | 4/2009 | Hitchcock | |
| 2011/0094516 A1 | 4/2011 | Chang | |
| 2012/0012113 A1 | 1/2012 | Chien | |
| 2013/0000646 A1 | 1/2013 | Haibach | |
| 2013/0133664 A1 | 5/2013 | Startare et al. | |
| 2015/0190600 A1 | 7/2015 | Zeijlstra | |

FOREIGN PATENT DOCUMENTS

| | | |
|---|---|---|
| EP | 2005986 A2 | 12/2008 |
| WO | 2012020359 A1 | 2/2012 |

* cited by examiner

View X

DEVICE FOR POSITIONING A PATIENT INTERFACE

CROSS-REFERENCE TO RELATED APPLICATIONS

The present application is a continuation of U.S. patent application Ser. No. 16/192,895, filed Nov. 16, 2018, which is a continuation of U.S. patent application Ser. No. 14/078,748, filed Nov. 13, 2013, which claims priority under 35 U.S.C. § 119 of German Patent Application No. 10 2012 022 355.2, filed Nov. 15, 2012. The entire disclosures of these applications are expressly incorporated by reference herein.

BACKGROUND OF THE INVENTION

1. Field of the Invention

The present invention relates to a device for positioning a patient interface on the head of the user.

2. Discussion of Background Information

Patient interfaces serve the purpose of delivering respiratory gas provided by the ventilation device to the patients. Patient interfaces can be realized in different embodiments, for example as nasal or full-face masks. The patient interface is typically connected to the ventilation device by means of a respiratory gas hose and is fixed on the head of the user.

Since the patient interface has to be worn hour after hour or night after night by the patient, high demands are made on the wearing comfort.

Along with the precise fit of the patient interface, the fastening and fixing on the head of the user is important in order to avoid unpleasant pressure points and perviousness or leakages.

To ensure secure positioning of the patient interface in the region of the face of a patient, and to reduce the forces which act on the face, patient interfaces are used with forehead supports. These types of forehead supports are often too complicated, however, for the patient and in the majority of cases cannot be adjusted without time and effort.

The forehead supports available to date on the market are frequently provided with complicated adjusting devices and are sometimes not self-explanatory. After removal—which is necessary to clean the mask thereof—the user has to note the latching position of the forehead support and has to re-adjust it time after time.

It would be advantageous to have available an adjusting device for a patient interface which enables simple positioning of the patient interface and improves the wearing comfort of the patient interface.

SUMMARY OF THE INVENTION

The present provides generally an adjusting device for a patient interface which allows precise, simple positioning on the face of a patient.

The present invention provides an adjusting device for a patient interface that is fixed on the head of the patient by means of a head harness. The device comprises a support body and at least one spring element. The patient interface has at least one harness receiving element and the tightening force of the head harness is transmitted onto the spring element by the harness receiving element such that the spring element is compressed.

In one aspect of the device, the support body may engage at least in part in a horizontal receiving element of the mask body.

In another aspect, a receiving element for the spring element may be arranged in the region of the receiving element and/or in the support body.

In yet another aspect of the device, the spring element, in the mounted state, may be introduced in part into the receiving element and in part into the guide and may consequently be covered over its entire length.

In a still further aspect, the guide may comprise lugs on its outside, which lugs may be arranged in a resilient manner on webs, and, when the support body is mounted, may engage with the lugs into the receiving region of the horizontal receiving element, and may latch there.

In another aspect, the guide elements, which engage in corresponding guide grooves inside the receiving element, may be situated on the outside of the spring receiving element for non-rotatable mounting.

In another aspect of the device of the present invention, the cylindrical receiving element may have an abutment face for the spring element on the end and the spring excursion may be defined by said abutment face and by the length of the receiving regions.

In another aspect, the spring element may be inserted at least in part into the opening of the forehead support receiving element and the face may lie in the undercut and may thus be held in the opening of the forehead support receiving element.

In another aspect, the cylindrical guide of the support body may be guided by the spring element and may be latched by way of the lugs in the receiving regions of the forehead support receiving element.

In another aspect, the spring element may abut against the abutment face in the support body and the spring excursion may be defined by the abutment face and by the chosen length of the receiving regions.

In another aspect, the spring element may comprise struts which are arranged in an X-shaped manner.

In another aspect, the spring element constant of the spring element may be in the range of from 0.1 to 2.0 N/mm, e.g., in the range of from 0.1 to 1.0 N/mm.

In another aspect, the characteristic curve of the spring element may be approximately linear and/or may have multiple stages as a result of the use of different elastomer materials and/or may have multiple stages as a result of the use of different geometries or geometric recesses (along the axis or transversely with respect to the axis) inside the spring element.

In another aspect of the device, the spring element may provide a spring excursion within the range of from 5 mm to 30 mm, e.g., from 7 mm to 20 mm.

In another aspect, the spring element may not be surrounded by the guide elements in a part region and may thus be accessible for cleaning.

In another aspect, the spring element may have an axis in the direction of which the spring may be compressed and/or the axis of the spring may be oriented substantially at right angles with respect to the forehead of the user.

In another aspect of the device, the spring element may have a first part region with a first characteristic (for example geometry or elasticity) at right angles with respect to the axis and a second part region with a second characteristic at right angles with respect to the first part region and with respect to the axis. The first characteristic may be different from the second characteristic.

In another aspect, the spring element may have a first part region and a second part region which are located opposite one another, the first part region having a greater degree of rigidity than the second part region.

In another aspect, a part region may have a greater degree of rigidity as a result of geometric structures (such as for example ribbing, an open or closed contour).

In another aspect, a part region may have a greater degree of rigidity as a result of different materials (which are joined using the two-component method and, for example, have different Shore hardnesses within the range of from A 20 to 80) and/or a may have a greater degree of rigidity as a result of different wall thicknesses.

The present invention also provides an adjusting device for a patient interface that is fixed on the head of the patient by means of a head harness. The device comprises a support body and at least one spring element, which spring element has an axis in the direction of which the spring element is compressed, and which spring element comprises a first part region with a first characteristic at right angles to the axis and, in a different location to the first part region, a second part region with a second characteristic.

The present invention also provides to an adjusting device for a patient interface that is fixed on the head of the patient by means of a head harness. The device comprises a support body and at least one spring element, the spring element constant of the spring element being in the range of from 0.1 to 2.0 N/mm.

The present invention also provides an adjusting device for a patient interface that is fixed on the head of the patient by means of a head harness. The device comprises a support body and at least one spring element, which spring element provides a spring excursion within the region of from 5 mm to 30 mm.

The present invention also provides a spring element for a patient interface. The spring element has an axis, and comprises a first part region with a first characteristic at right angles with respect to the axis and, in a different location to the first part region, a second part region with a second characteristic.

The invention further provides an adjusting device for a patient interface that is fixed on the head of the patient by means of a head harness. The device comprises a support body and a receiving element for the support body. A spring element is arranged between the support body and the receiving element, and harness receiving elements transmit the tightening force of the head harness at least in part onto the spring element.

In one aspect of the device, the spring element may enable stepless adjustment.

In another aspect, the spring element may provide a spring excursion within the range of from 7 mm to 20 mm, e.g., from 7 mm to 17 mm.

In yet another aspect, the support body may engage at least in part in the horizontal receiving element of the mask body.

In a still further aspect of the device, the support body may reach at least in part over the horizontal receiving element of the mask body.

In another aspect, the restoring force of the spring element and the restoring force of the forehead support pad may be designed in such a manner that, when the harness is tightened, first of all the forehead support pad adapts to the form of the forehead of the user and only then is the spring element compressed.

In another aspect, the spring element may be fixed in the region of the receiving element.

In another aspect, the spring element may be fixed in the support body in the region of the cylindrical guide.

In another aspect, the spring element in the mounted state may be introduced in part into the receiving element and in part into the cylindrical guide and may consequently be completely covered.

In another aspect, the spring element in the mounted state may be introduced in part into the receiving element and in part into the cylindrical guide and may consequently be covered in part.

In another aspect, the cylindrical guide may be introduced at least in part into the receiving element and may be fixed there so as to be releasable.

In another aspect of the device, the cylindrical guide may have lugs on the outside, which lugs are arranged in a resilient manner on webs, and, when the support body is mounted, may engage with the lugs in the receiving regions of the cylindrical horizontal receiving element and may lightly latch there.

In another aspect, the guide elements which engage in corresponding guide grooves inside the receiving element and are guided there, may be situated on the outside of the cylindrical spring receiving element for non-rotatable mounting.

In another aspect, the cylindrical receiving element may have an abutment face for the spring element on the end and the spring excursion may be defined by said abutment face and by the length of the receiving regions.

In another aspect of the above device, the spring element may be inserted at least in part into the opening of the forehead support receiving element and the face may lie in the undercut and may thus be held in the opening of the forehead support receiving element.

In another aspect, the cylindrical guide of the support body may be guided by means of the spring element and may latch with the lugs in the receiving regions of the forehead support receiving element.

In another embodiment, the spring element may abut against the abutment face in the support body and the spring excursion may be defined by the abutment face and by the chosen length of the receiving regions.

In another aspect, the elastomer spring may obtain its function as a compression spring as a result of the X-shaped arrangement of the struts and the selection of the material.

In another aspect, the spring element constant may be from 0.1 to 2.0 N/mm, in a preferred manner from 0.1 to 1.0 N/mm, in a particularly preferred manner from 0.1 to 0.8 N/mm or even in the range of from 0.1 to 0.5 N/mm.

Depending on the tightening force of the harness of the head harness or of the head cap and on the shape of the face of the user or of the forehead of the user, the spring element inside the forehead support is compressed more or less tightly and presses the forehead pad onto the forehead of the user and thus always provides the patient interface at the spacing that is suitable for the patient.

BRIEF DESCRIPTION OF THE DRAWINGS

The following Figures show non-limiting exemplary embodiments of a patient interface having a support body of the type set forth at the outset. In particular, the Figures show.

DETAILED DESCRIPTION OF EMBODIMENTS OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
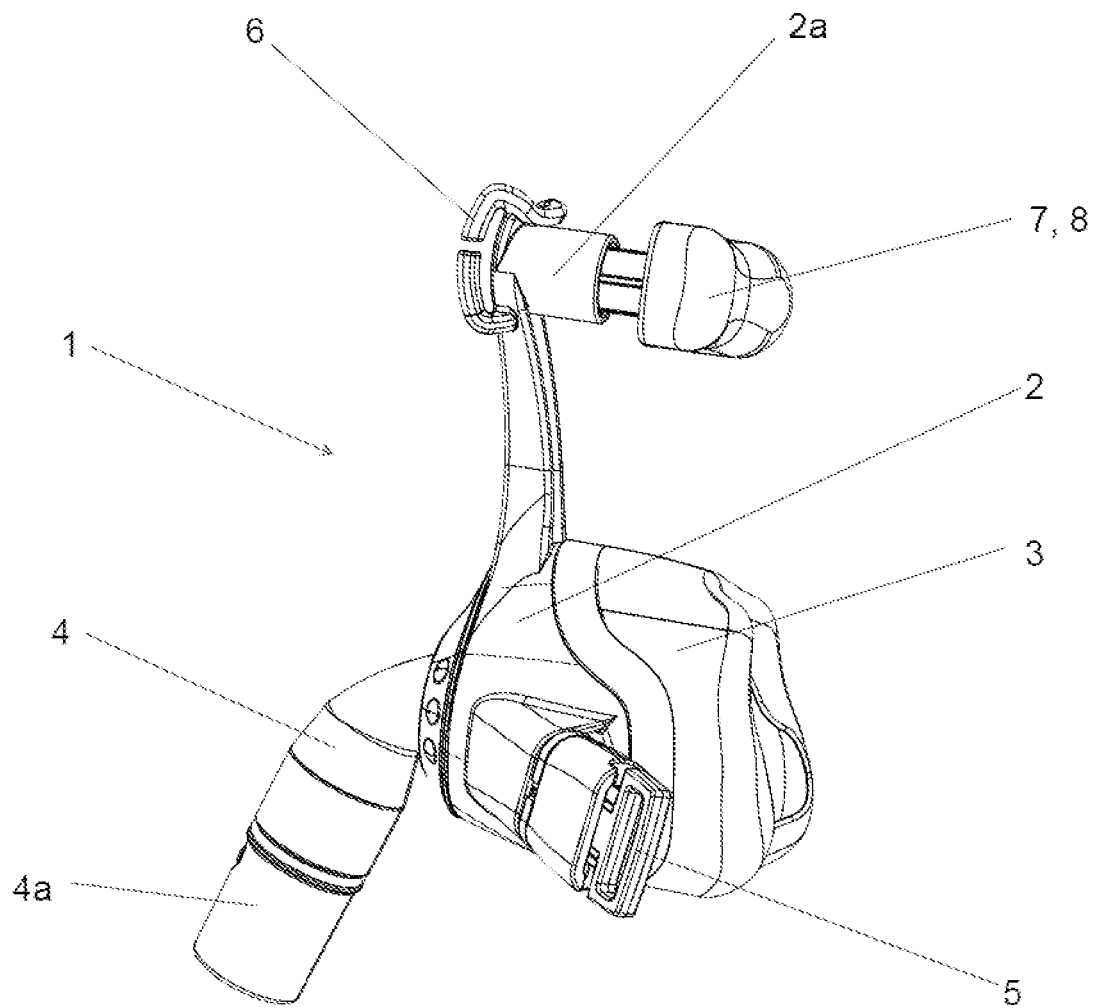
FIG. 1: Patient interface
Figure 1A:
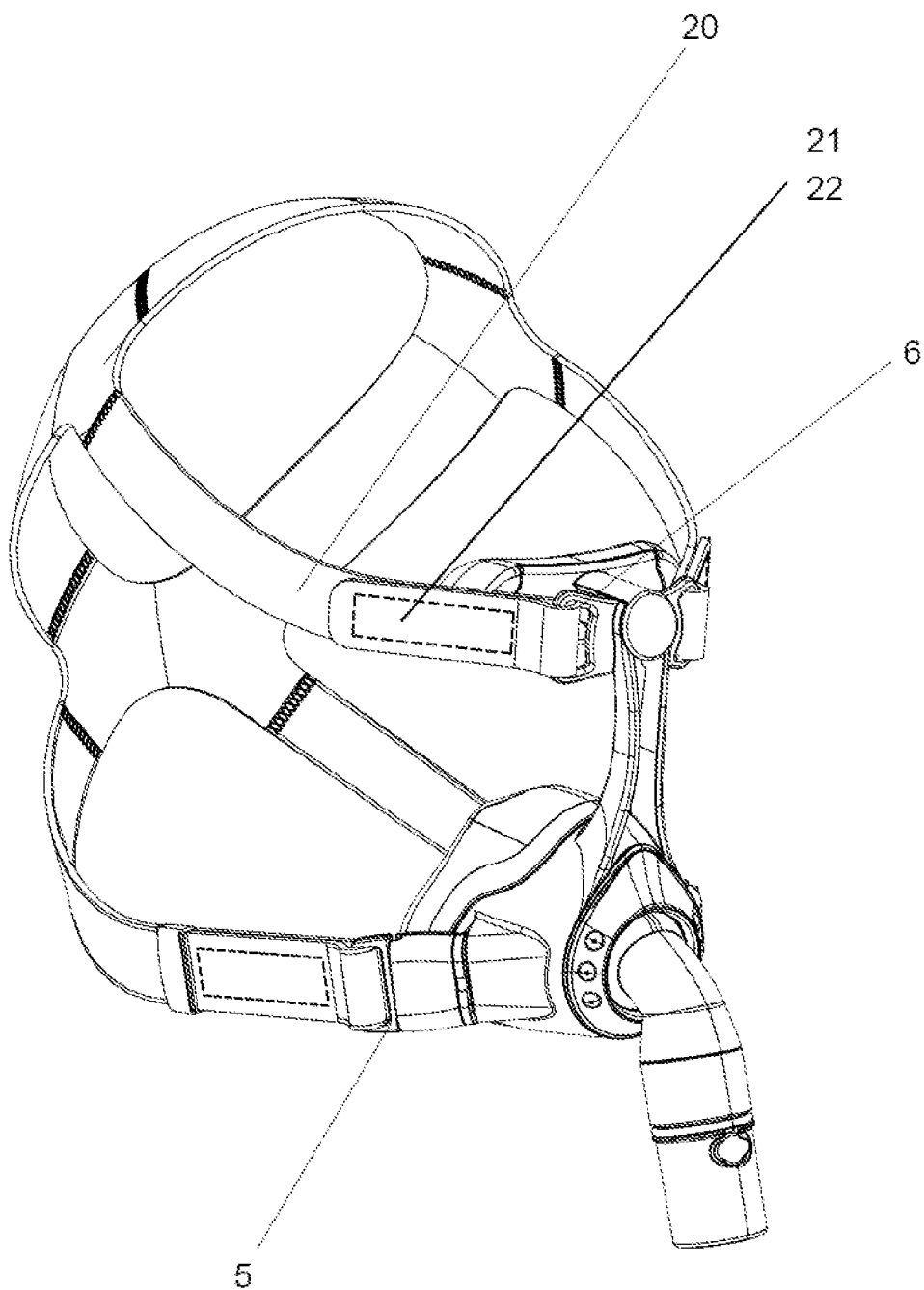
FIG. 1a: Patient interface with harness

FIGS. 1 and 1a show a patient interface (1). The patient interface (PI) has a mask body (2), on which the respiratory gas hose (not shown) is connected to the PI by means of a ball-and-socket joint (4) and a rotary sleeve (4a). The mask body (2) has a sealing element (3) in the form of a mask bead with a lip seal as means for sealing in relation to the face of the patient. Fixing in the region of the head of a patient can be effected by means of a head cap or head harness (20). The harness ends (22) of the head cap or head harness are releasably fastened on the PI on the one hand by means of a receiving element (5) in the cheek region and on the other hand by means of receiving element (6) in the forehead region. For this purpose, the harness ends (22) are guided through the receiving element (6) and are fixed on the harness by means of a Velcro fastening (21). The receiving element (6) has a slot for inserting the harness. A support body (7) with a forehead support pad (8) serves for supporting the patient interface (1) in the region of the forehead of the patient. The support body (7) engages in the horizontal receiving element (2a) of the mask body (2).

Figure 2:
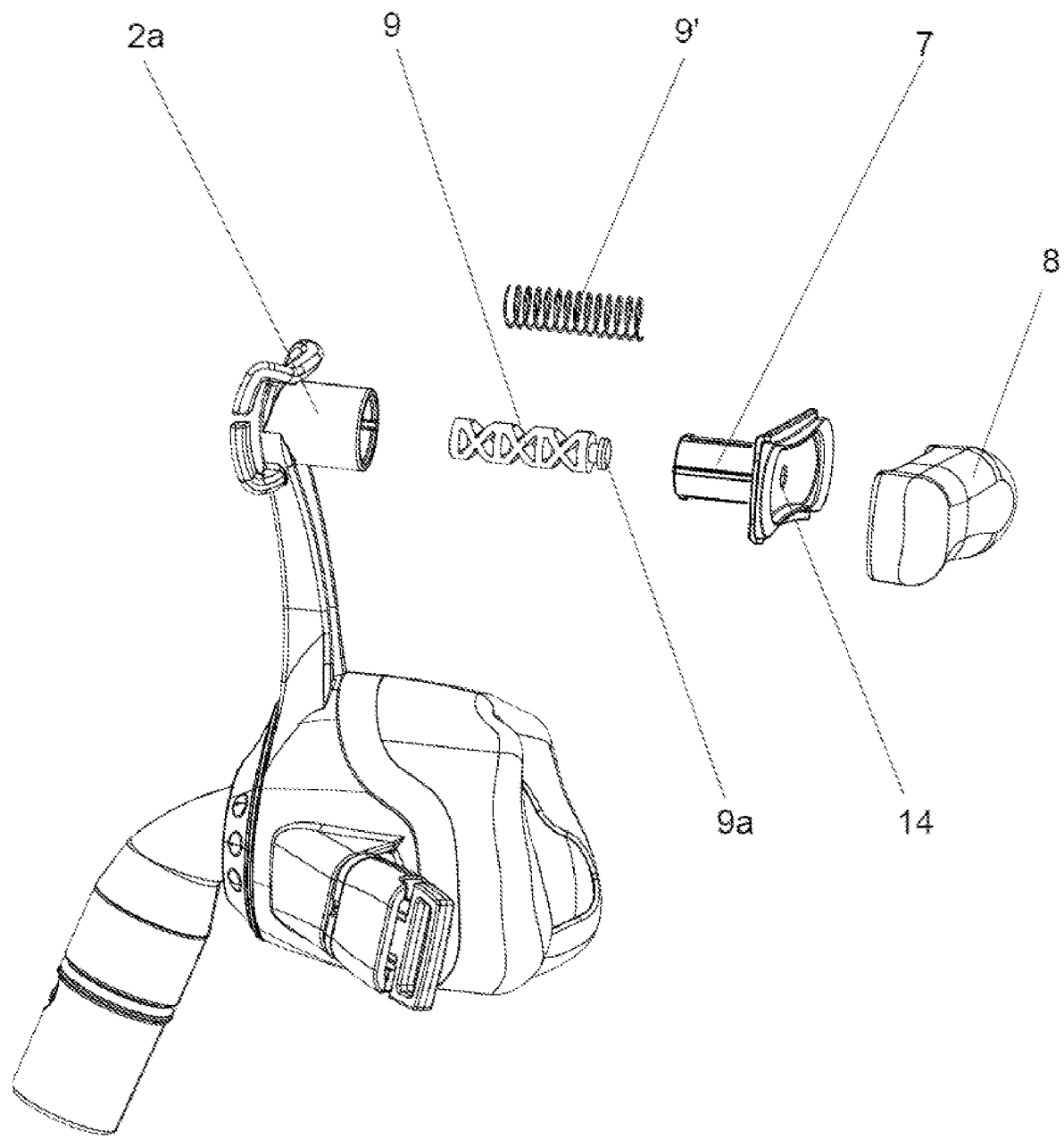
FIG. 2: Exploded representation of the forehead support adjusting element, variant 1

FIG. 2 shows that the support body (7) of the forehead support has on the side of the patient a forehead pad (8) which is produced from a silicone that is kind to the skin and can also be provided with a gel filling. A cylindrical guide (10) (see FIG. 3) serves to receive the spring element (9, 9'). The spring element (9) is inserted into the receiving element (10), in the bottom of which an additional opening (14) is arranged in which the spring element is held by means of a mushroomed thickening (9a) and a circumferential undercut (9b) such that the spring element (9) cannot be lost when being disassembled or during the daily cleaning of the mask. A comparable safety device can be provided as a compression spring (9').

Automatic adjustment/re-adjustment of the support body (7) is effected by means of a spring element (9, 9') located inside the support body. The spring element can also be arranged outside in all the exemplary embodiments, for example as a forehead support pad. The spring element can be realized as an elastomer spring (9) (see FIGS. 5, 9, 13 and 14) produced from an elastomer such as, for example, silicone or TPE, or from different elastomers which are joined together or as an alternative to this as a compression spring (9') produced of metal, such as high-grade steel, or of plastics material, such as POM. A compression spring produced of POM can be a cost-effective alternative to the compression spring of high-grade steel.

Depending on the tightening force of the head harness, the spring element (9, 9') is compressed inside the support body more or less tightly and presses the forehead support pad onto the forehead of the user and thus always provides the patient interface at the optimum spacing which is suitable for the patient. Even when the patient alters his position in sleep, the spring element (9, 9') compensates again for the change.

The spring force of the spring element (9, 9') and the force of the forehead support pad (8) can be designed such that, when the harness is tightened, first of all the forehead support pad (8) is adapted to the shape of the face of the user or of the forehead of the user and only then does the spring force of the spring element (9, 9') become active. The spring forces of the spring element (9, 9') and of the forehead support pad (8) can also be the same. It is also possible for the spring force of the spring element (9, 9') to be less than that of the forehead support pad (8).

Figure 3:
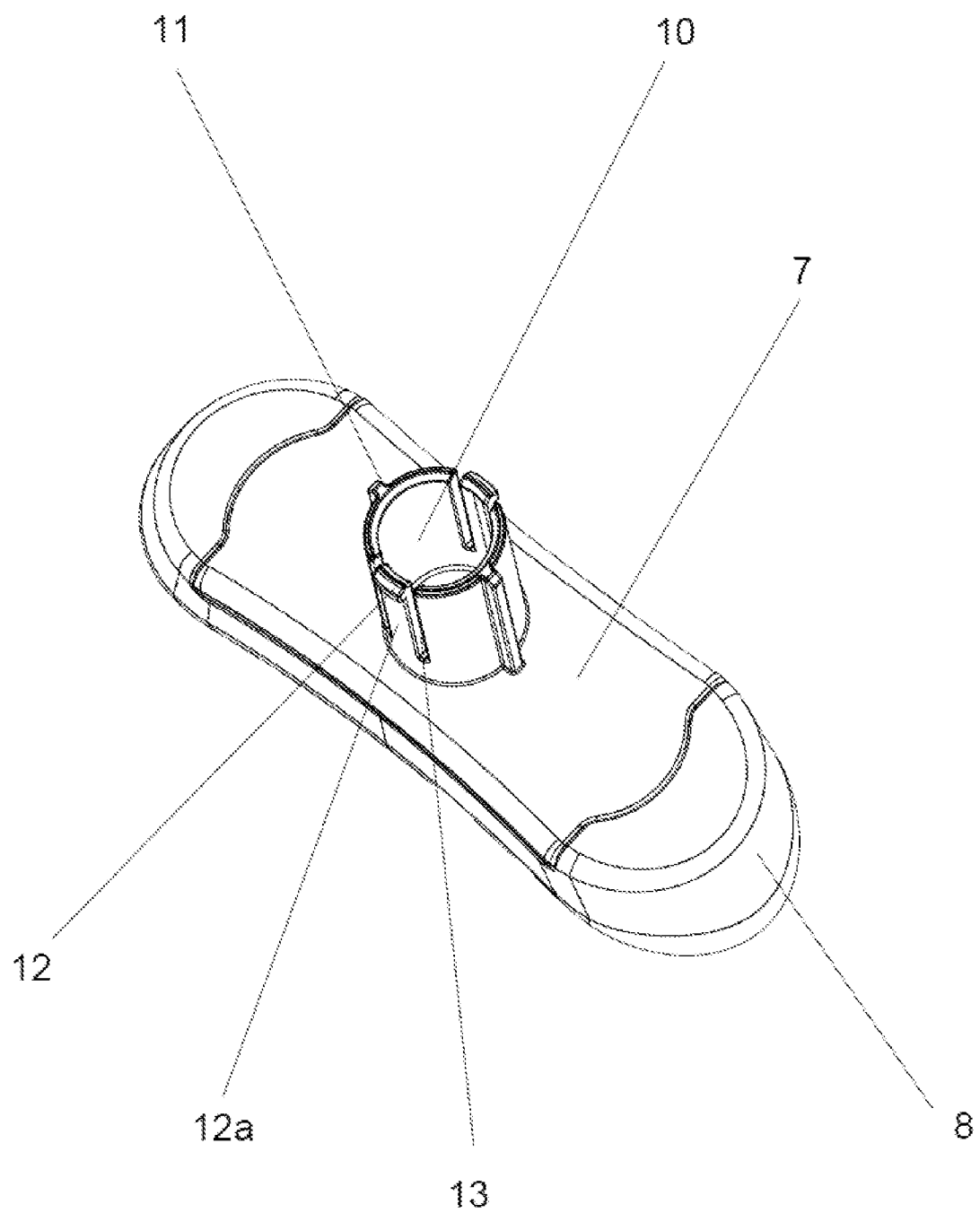
FIG. 3: Forehead support

FIG. 3 shows that the cylindrical guide (10) has lugs (12) on the outside which—brought about by the slot (13) in the guide (10)—are arranged on webs (12a). The webs (12a) are lightly resilient and, when the support body is mounted, engage with the lugs (12) in the receiving regions (17) of the equally cylindrical receiving means of the support body (2a) and latch there. Said latching prevents the forehead support being able to slip out in an unwanted manner. Guide elements (11), which engage in corresponding guide grooves (16) inside the receiving element (2a) and are guided there, are situated on the outside of the cylindrical spring receiving element (10) for non-rotatable mounting.

Figure 4:
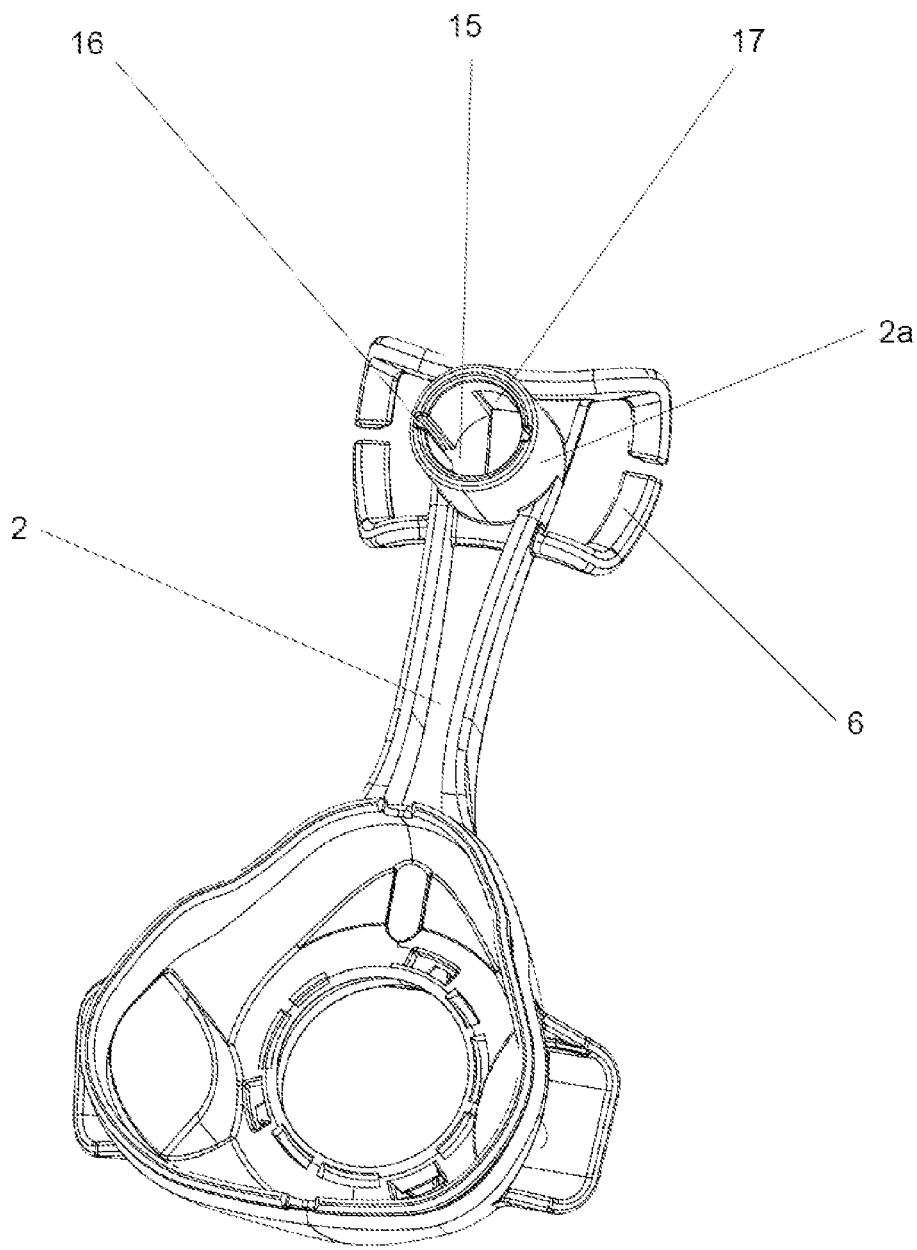
FIG. 4: Mask body

FIG. 4 shows the cylindrical receiving means (2a) which has an abutment face (15) for the spring element (9, 9') on the end. The spring excursion (24) is defined by the abutment face (15) and by the chosen length of the receiving regions (17). In one exemplary embodiment, the guide (10) slides in a telescopic manner in the receiving region (17), both completely covering the spring element.

Figure 5:
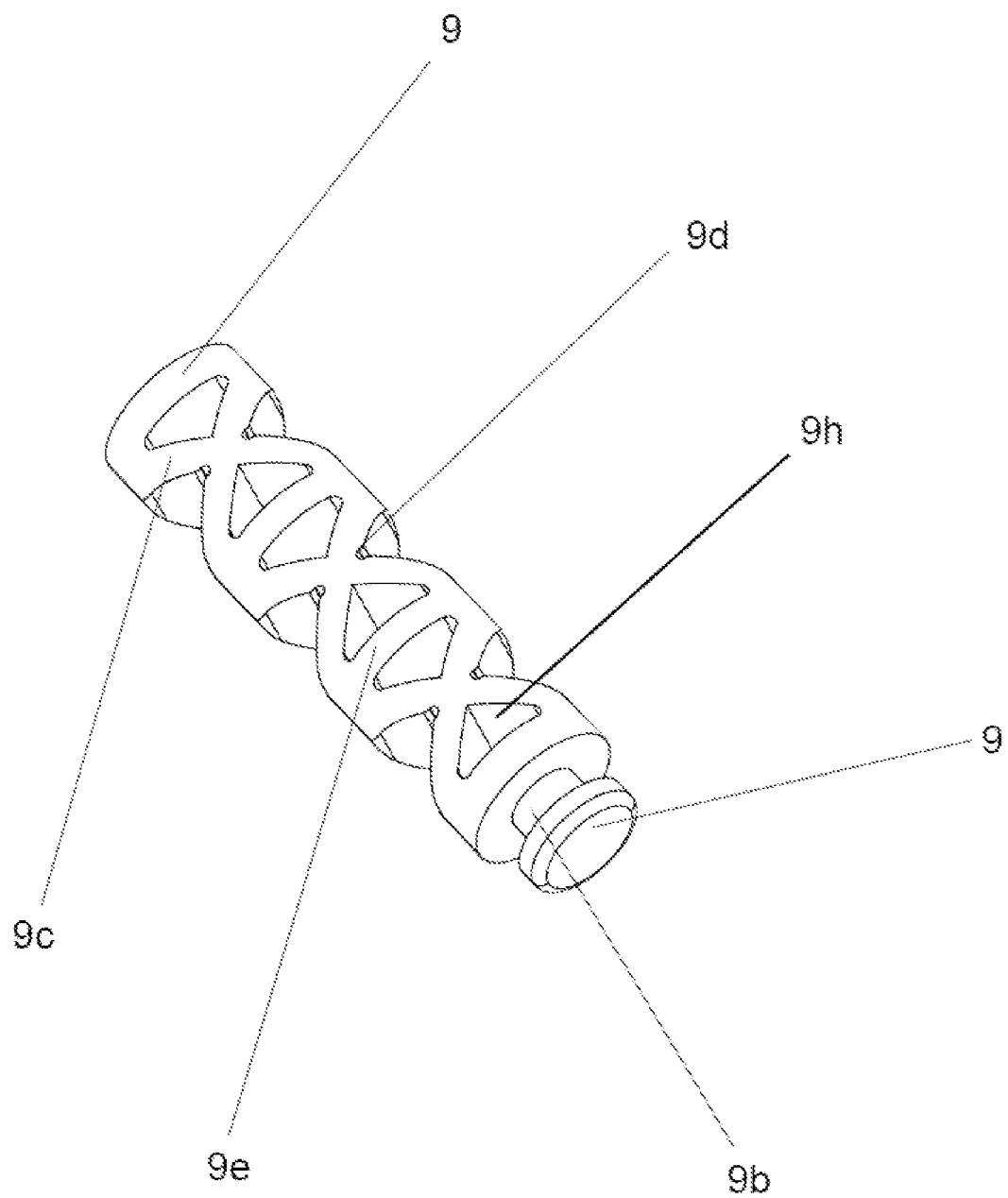
FIG. 5: Elastomer spring

FIG. 5 shows the spring element as an elastomer spring (9). The elastomer spring (9) obtains its function as a result of the X-shaped arrangement of the struts (9c) and the selection of the material. When pressure is applied to the spring element (9), the angle in the X-shaped spring structure is altered and the spring element becomes shorter. Relief cuts (9d) in the X-shaped struts and those between the X-shaped struts (9d) prevent the elastomer spring (9) from deforming under pressure. The relief cuts (9h), triangular in this case, expose a spring space. In principle, the spring characteristic can be influenced as a result of the geometry and shape of such relief cuts (9h).

Figure 6:
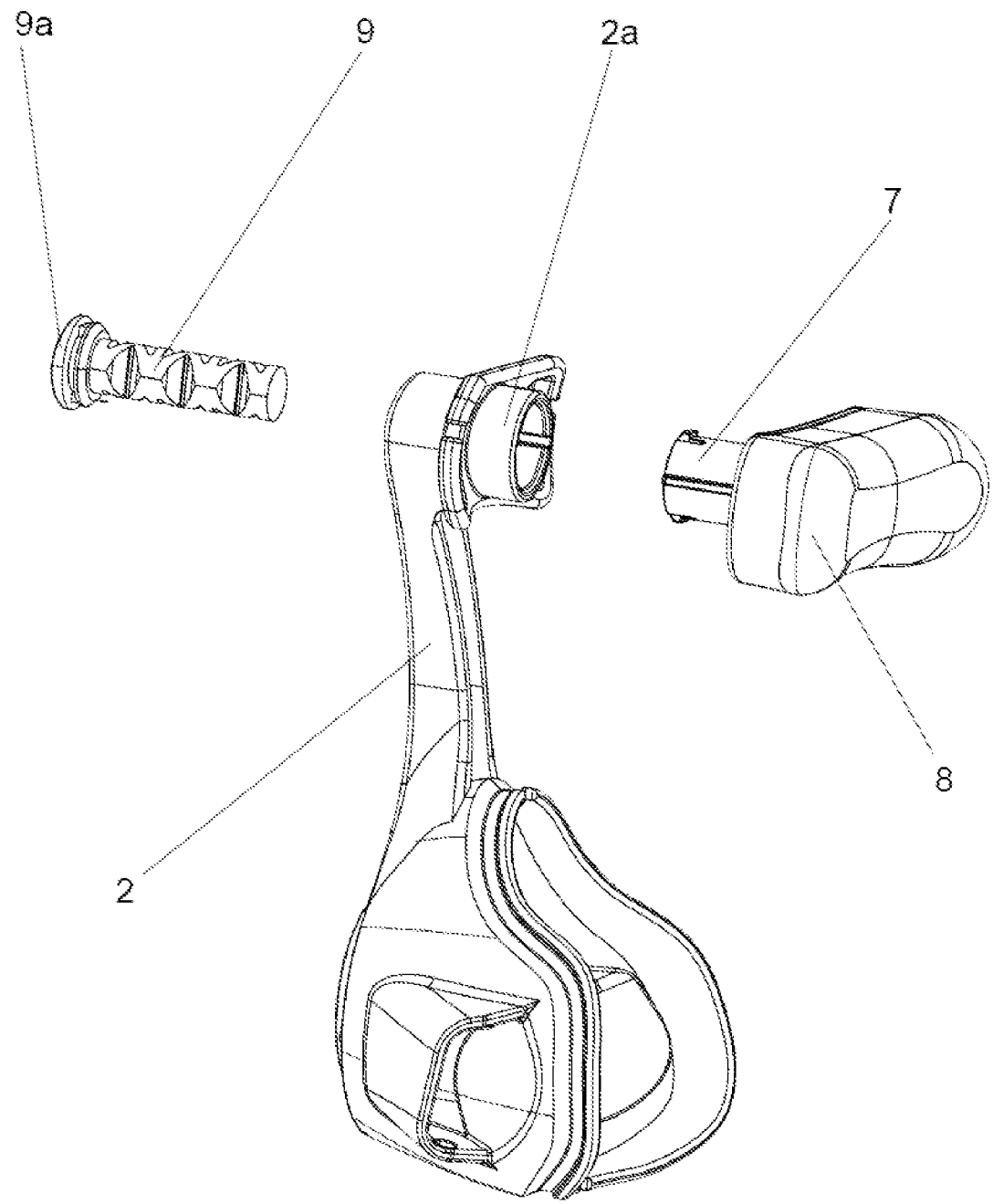
FIG. 6: Exploded representation of the forehead support adjusting element, variant 2
Figure 7:
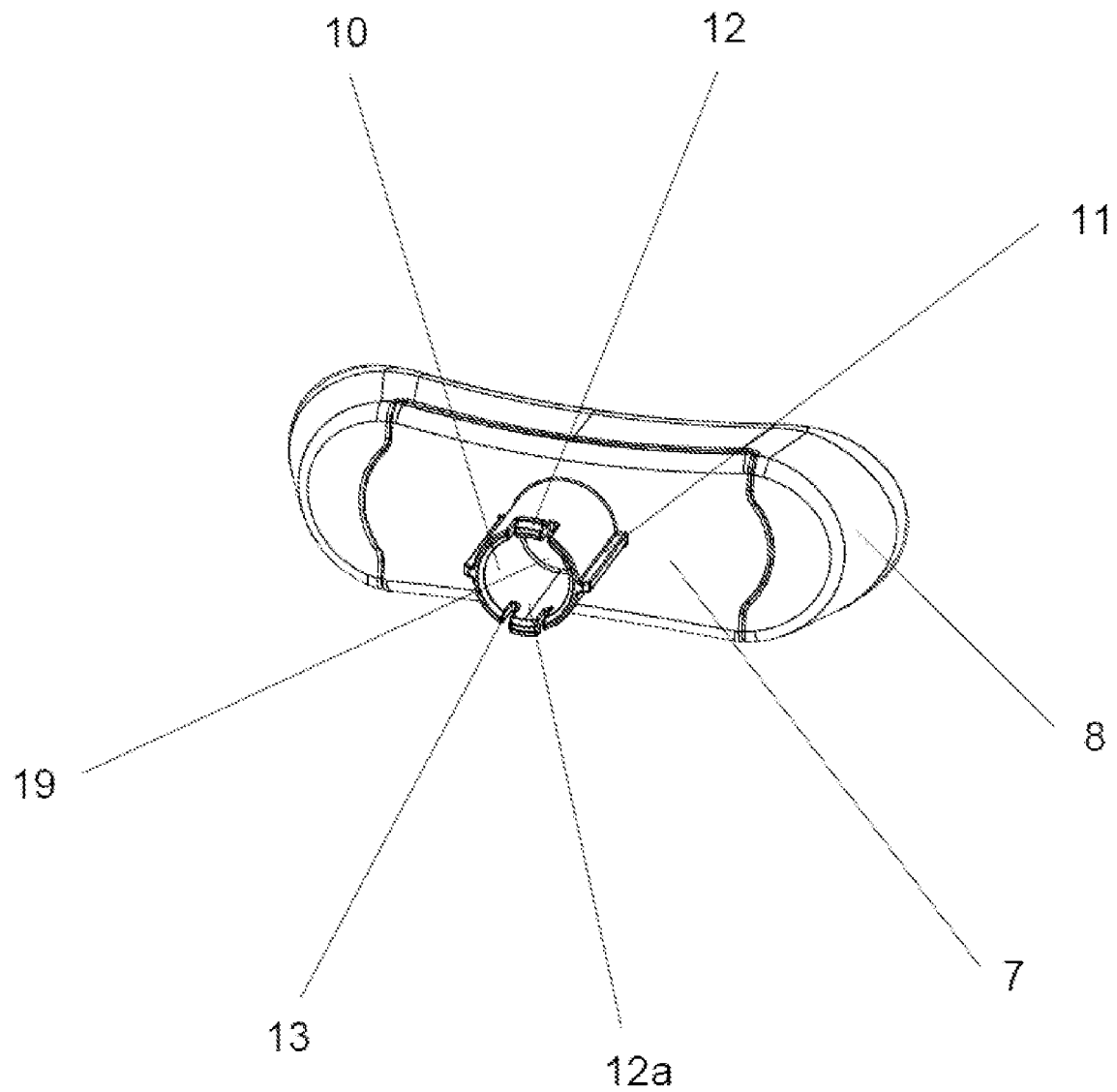
FIG. 7: Forehead support
Figure 8:
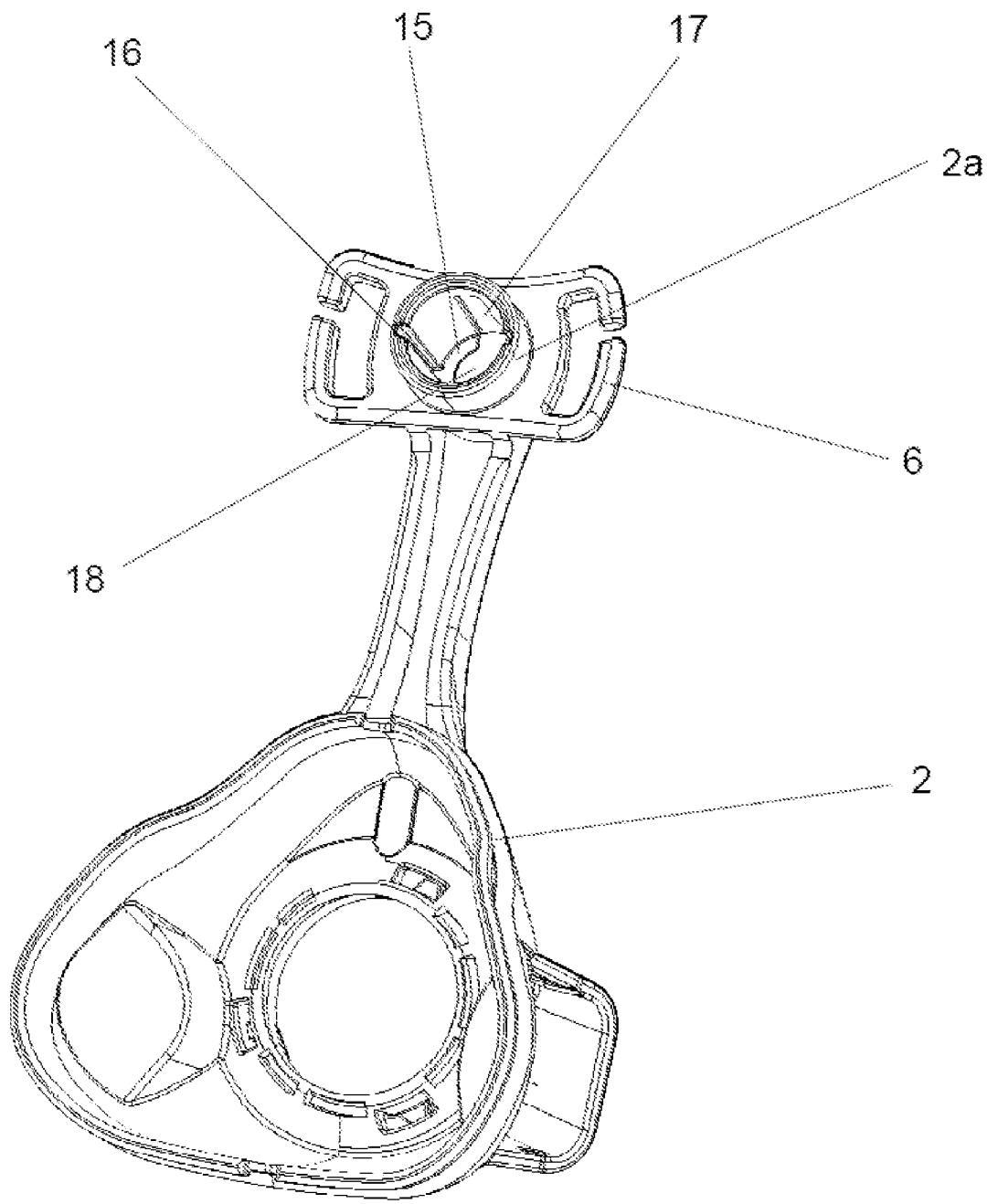
FIG. 8: Mask body
Figure 9:
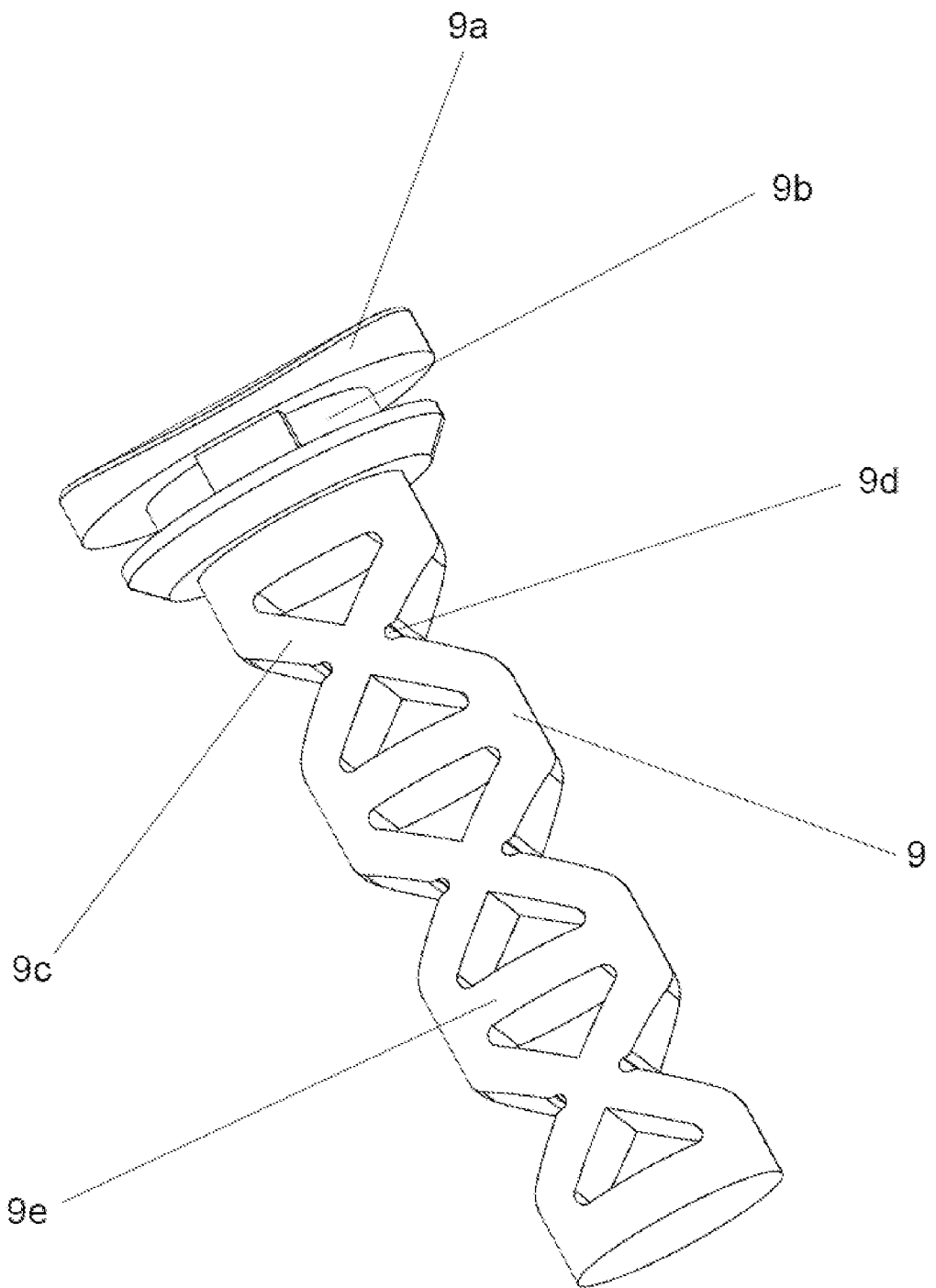
FIG. 9: Elastomer spring

FIG. 6 shows an exploded representation of the assembly. FIGS. 7 to 9 show the corresponding individual parts. The difference to the first variant is the elastomer spring (9) which in said embodiment is not held in the opening (14) in the support body (7), but is held by way of its thickening (9a) and an undercut (9b) in the opening (18) of the forehead support receiving element (2a). For assembly, the elastomer spring (9) is inserted from the front into the opening (18) of the forehead support receiving element (2a) and is pulled until the face (15) lies in the undercut (9b). The cylindrical guide (10) of the support body (7) is then guided by means of the spring element and also latches, as has already been described in variant 1, with the lugs (12) in the receiving regions (17) of the forehead support receiving element (2a). The elastomer spring (9), in said variant, abuts against the abutment face (19) in the support body (7). The spring excursion (24) is defined by the abutment face (19) and by the chosen length of the receiving regions (17).

Figure 10:
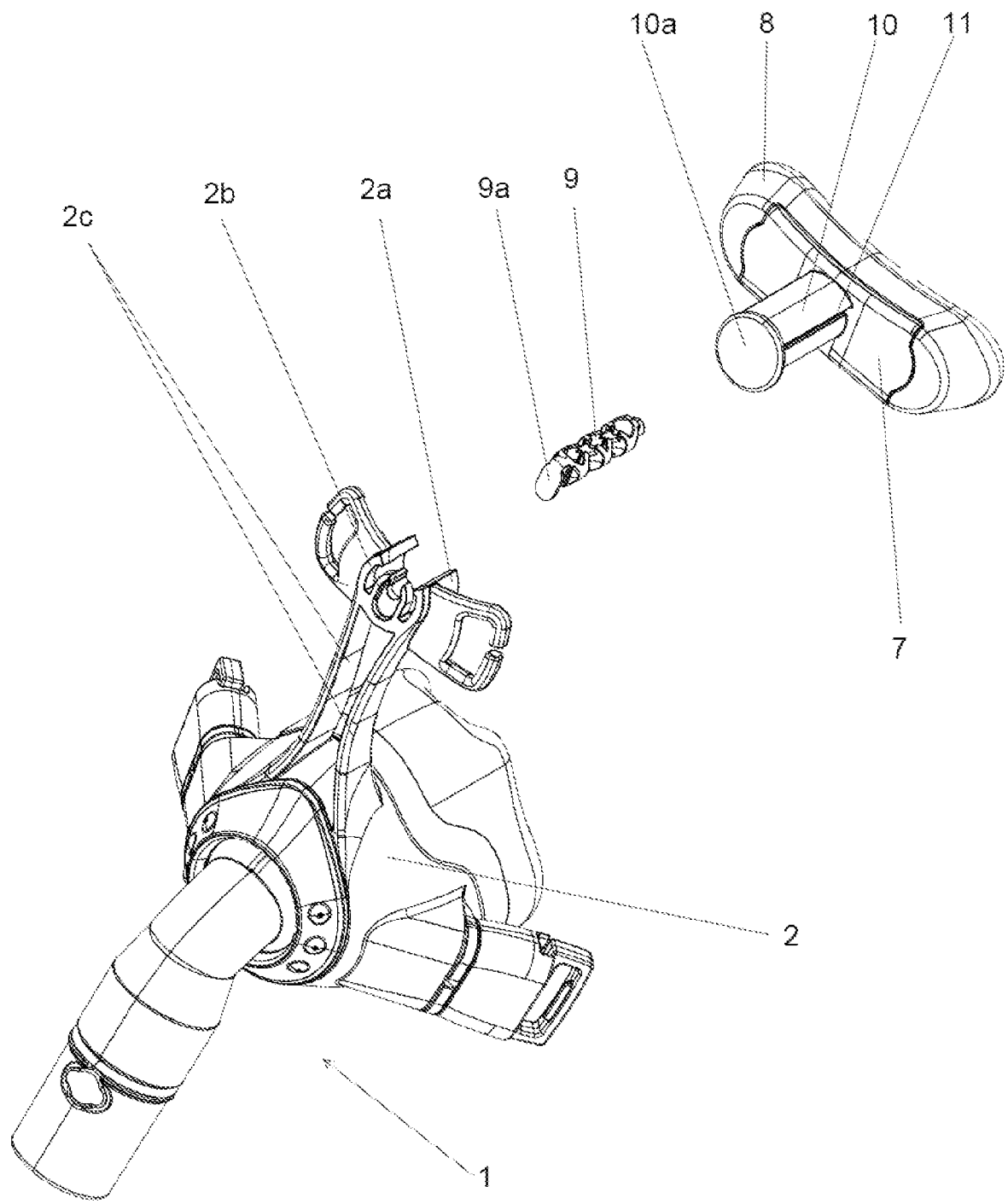
FIG. 10: Exploded representation of the forehead support adjusting element, variant 3
Figure 11:
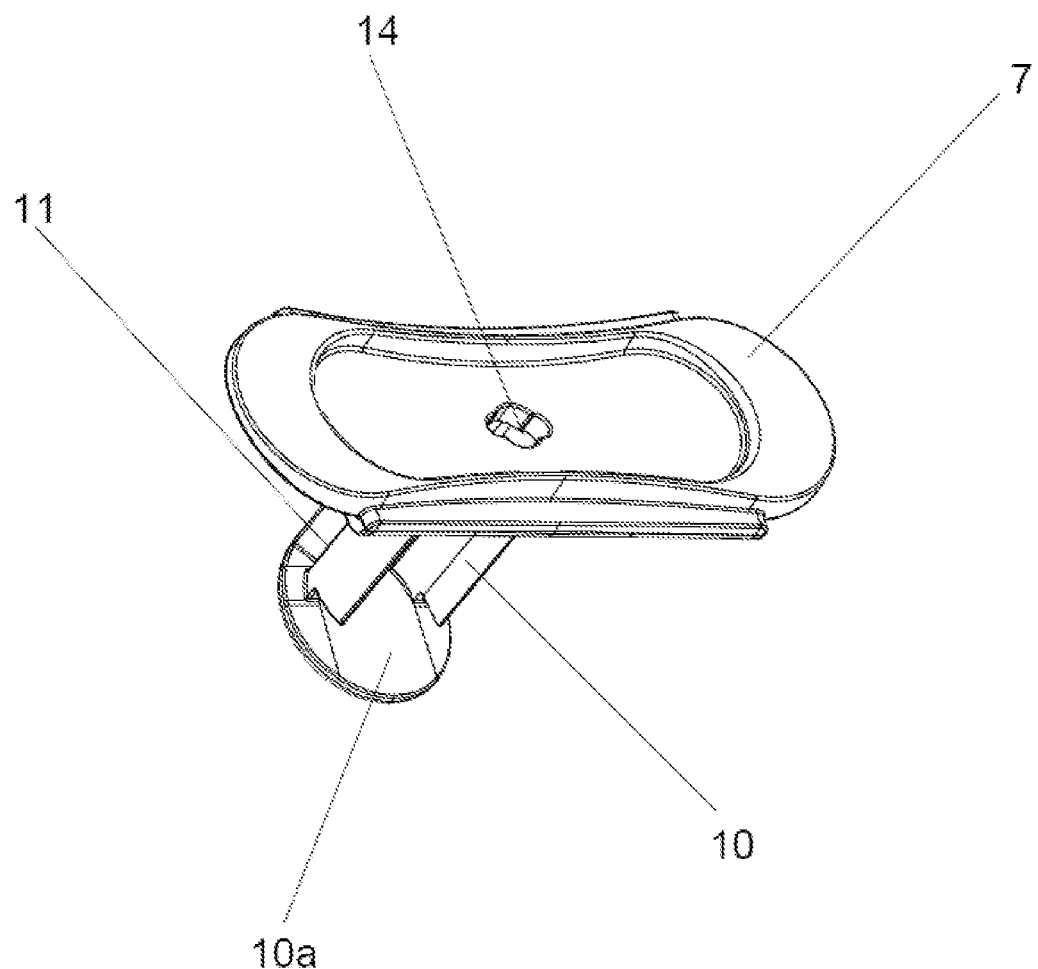
FIG. 11: Forehead support
Figure 12:
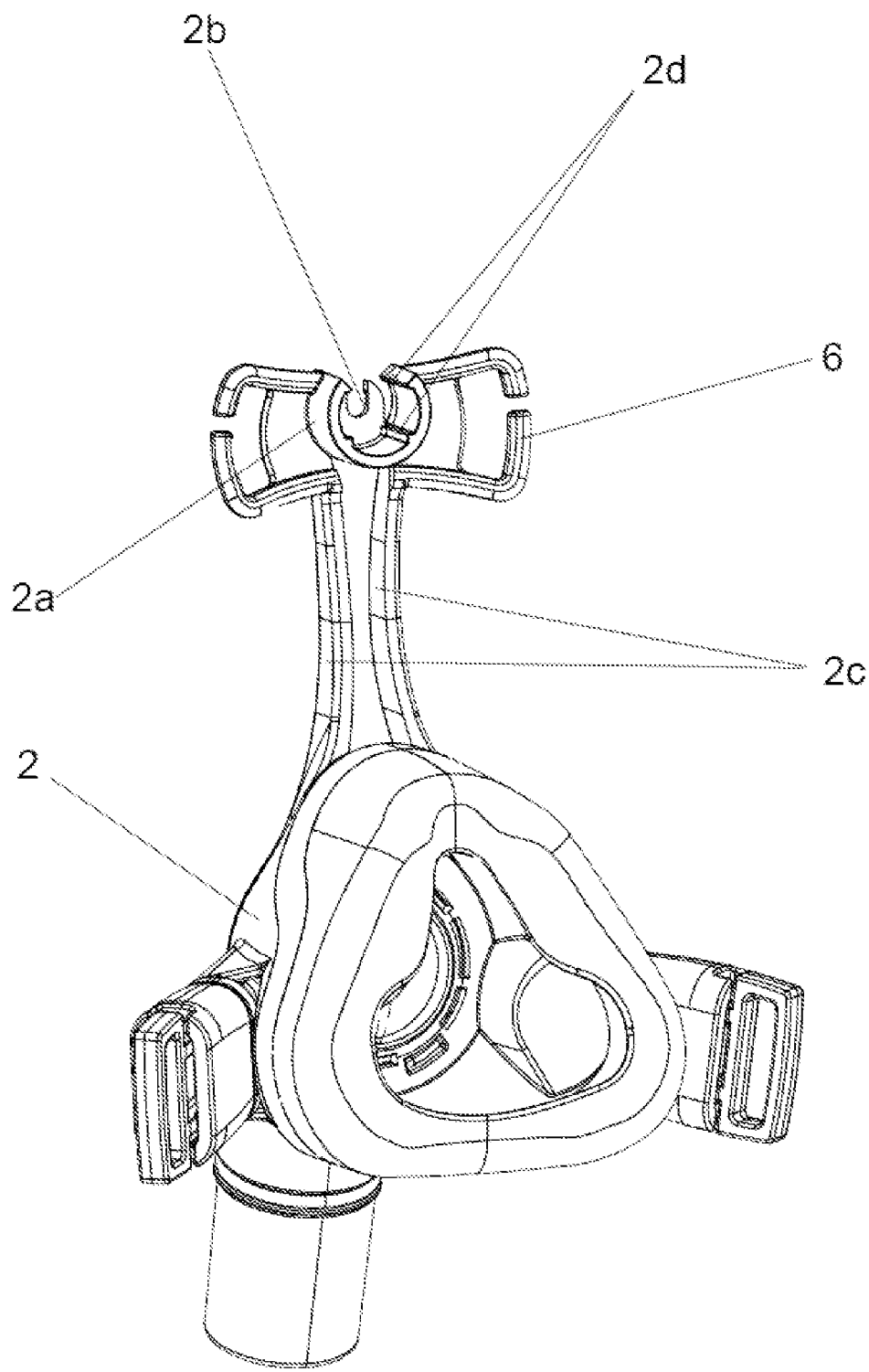
FIG. 12: Mask body
Figure 13:
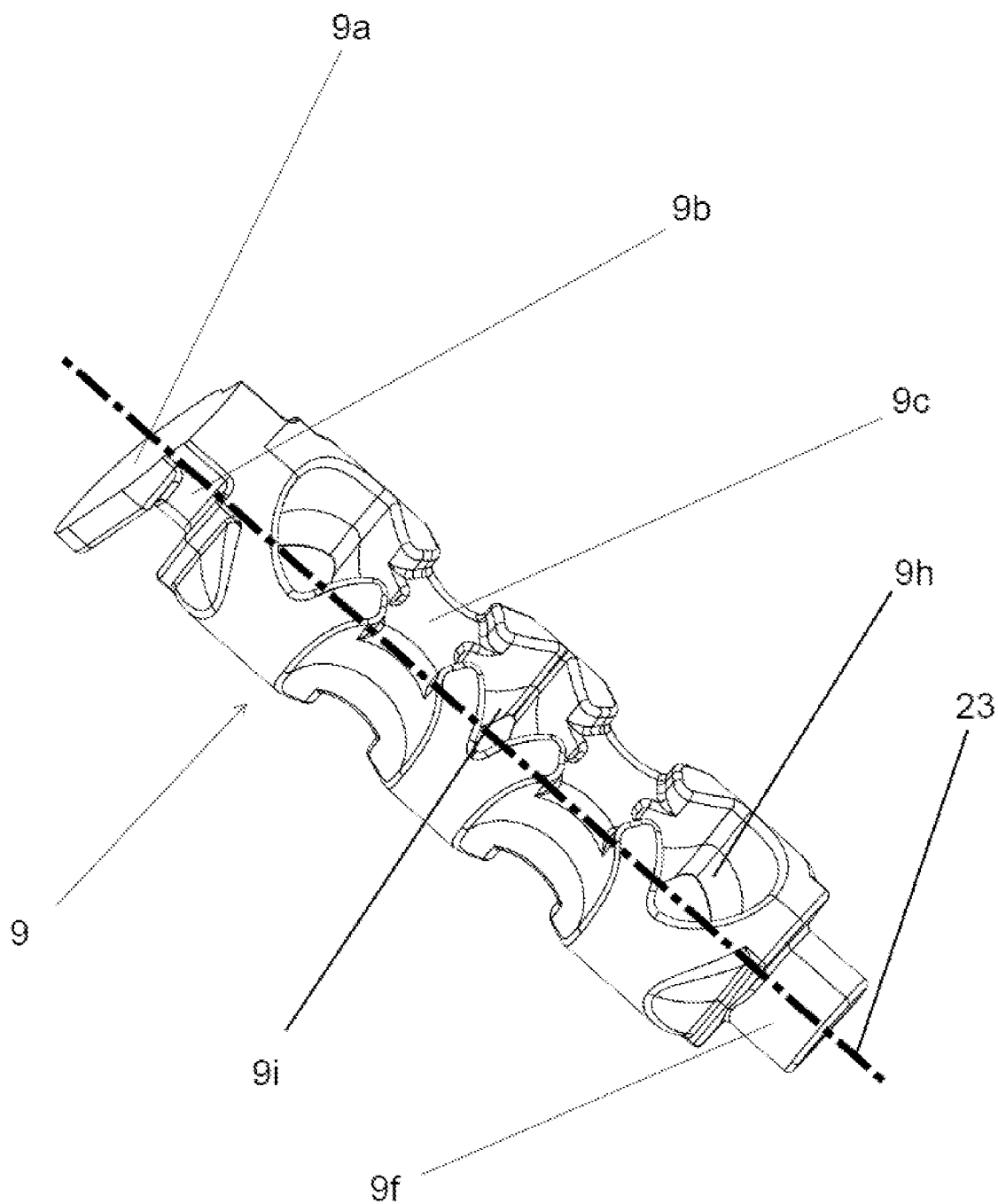
FIG. 13: Elastomer spring element

FIG. 10 shows a further embodiment for positioning a forehead support of a patient interface (1) by means of a spring element (9). The corresponding individual parts are shown in FIGS. 11 to 13. For assembly, the spring element (9) is linked into the receiving region (2b) of the receiving element (2a) by means of a plate (9a) and an undercut (9b). The spring element (9) has on the opposite end a centering element (9f) which is inserted into the opening (14) in the abutment face (19) of the support body (7) and prevents the spring element (9) moving sideways or slipping in the support body.

The connecting webs (2c) between the mask body (2) and the receiving region of the forehead support (2a) are configured such that they preferably make compression possible and as a result widen the receiving region (2a) and enable the mounting of the support body (7).

For mounting, the two connecting webs (2c) are compressed and the support body is clicked into the opening of the receiving element (2a). In this case, the centering element (9f) of the spring element (9) has to be positioned correctly in the opening (14). It is ensured that the support body (7) is rotationally fixed as a result of guide elements in the form of a shoulder (11) on the circumference of the spring element receiving means (10) of the support body (7) and chamfers (2d) in the receiving means (2a).

The plate (10a) on the support body (7), which, in the mounted state, lies in front of the receiving element of the support body (2a), forms a stop in the direction of the patient at that location. The adjusting path of the support body is defined by the abutment of the spring element (9) in the support body (7) and by the length of the spring element receiving element (10) on the support body. The minimum adjusting point of the support body (7) with respect to the forehead of the patient is achieved when the plate (10a) abuts at the front against the receiving element of the support body (2a). The maximum adjusting point of the support body (7) is achieved when the receiving element (2a) abuts against the support body (7).

FIG. 13 shows the spring element as an elastomer spring (9). The elastomer spring (9) has an axis (23) in the longitudinal direction thereof. Force is always applied in the direction of the axis (23). The elastomer spring (9) obtains its function as a result of the arrangement of the struts (9c) and relief cuts (9h, 9i). When pressure is applied onto the spring element (9), the angle in the relief cuts (9h, 9i) is altered and the spring element becomes shorter. The different relief cuts here (9h, 9i) in each case form a spring space. In this case the geometry is chosen such that the relief cut (9i) is softer and consequently deflects immediately when force is applied onto the spring element. The relief cut (9h), as a result of the geometry thereof deviating from the relief cut (9i), is harder and consequently does not deflect fully until after the relief cut (9i). In principle, the spring characteristic can be influenced as a result of the geometry and shape of such relief cuts (9h, 9i).

Figure 14:
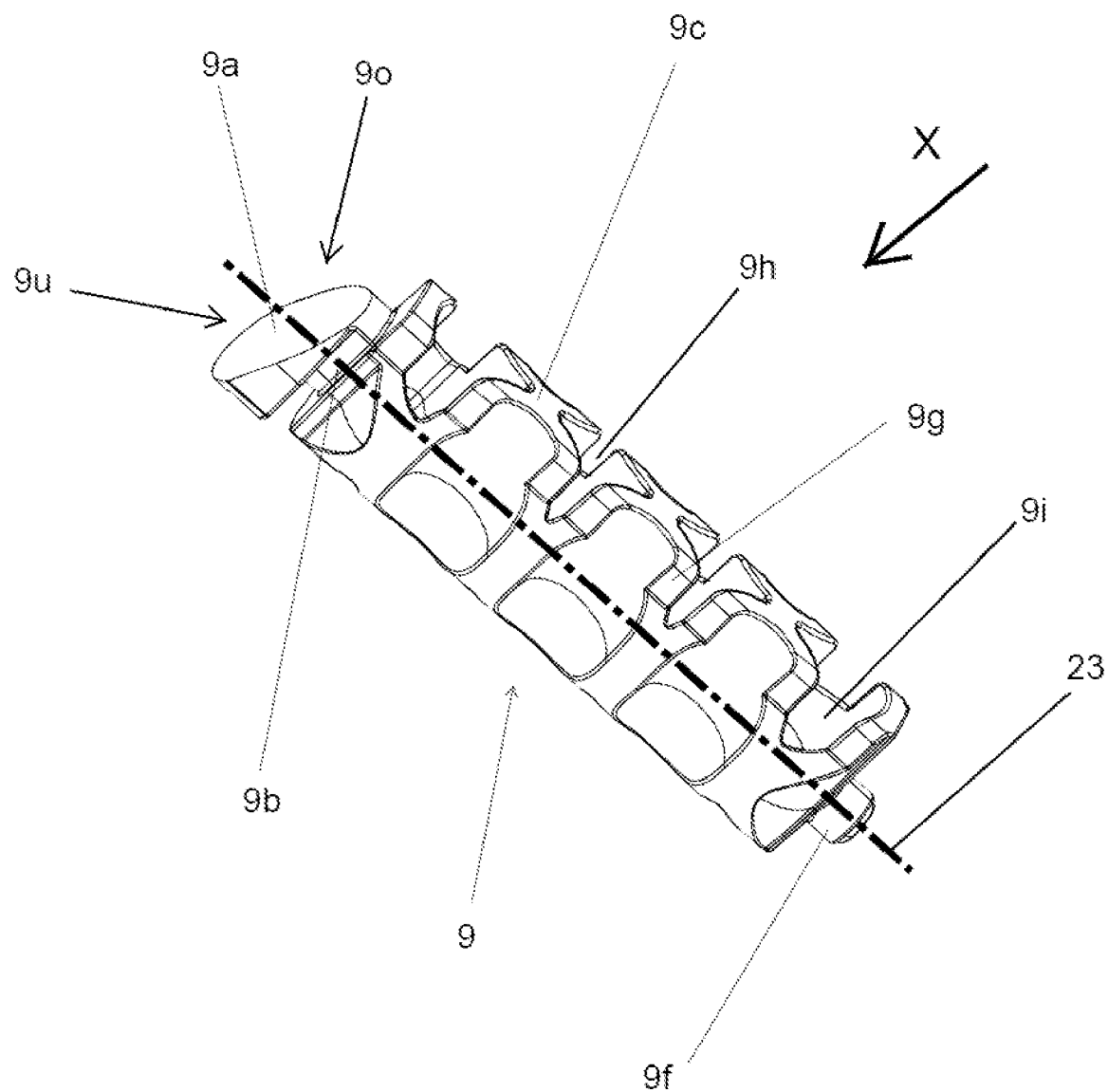
FIG. 14: Spring element, view from the side
Figure 14A:
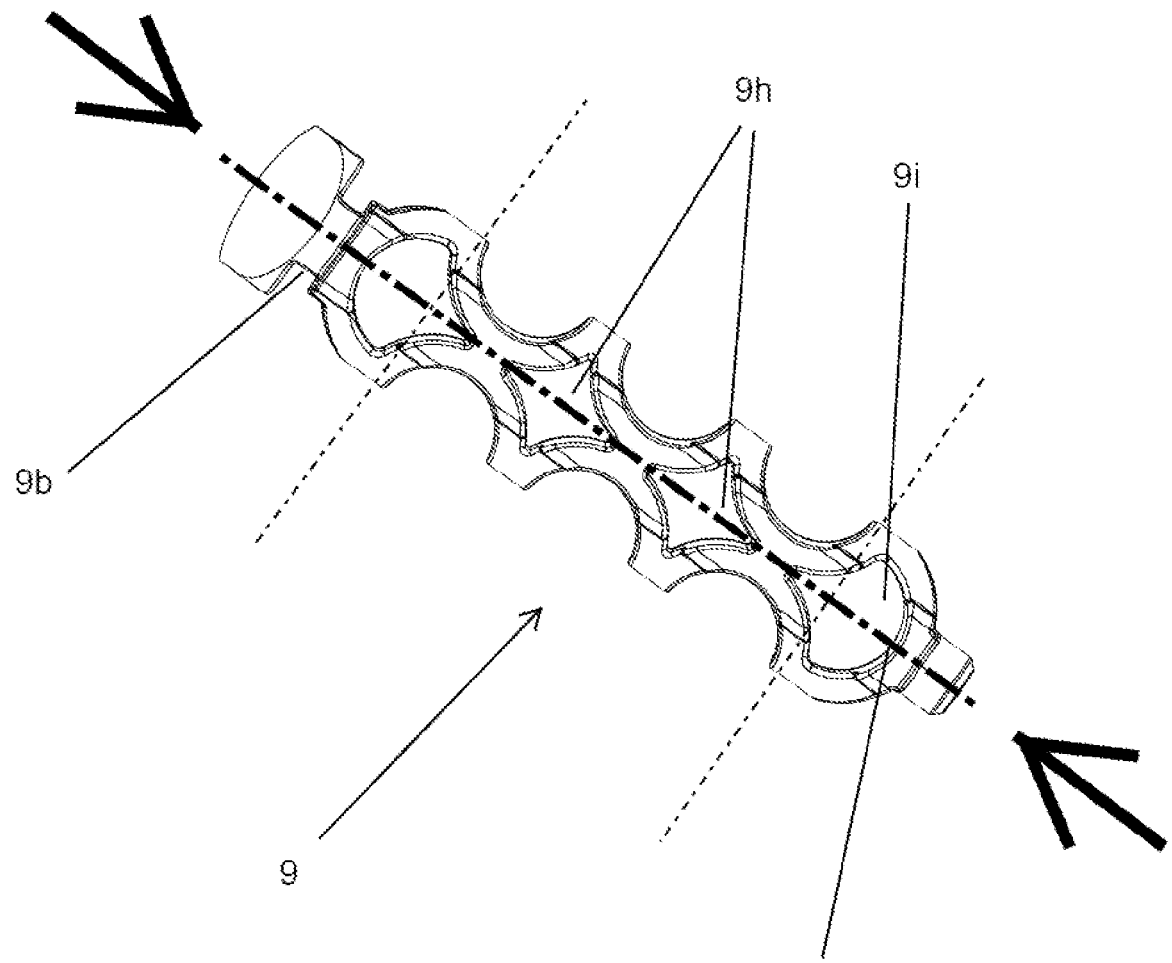
FIG. 14a: Spring element, view from above

FIGS. 14 and 14a show the spring element which has, at right angles with respect to the axis (23), a first part region (9h), in this case realized as a result of the relief cut as a square geometric recess, with a first characteristic which, in this case, is realized as a higher spring constant or as a harder portion. A second part region (9i) is realized away from the location of the first part region, in this case as a result of the relief cut as a triangular geometric recess (with a rounded base), which has a second characteristic. The second characteristic, in this case, is realized as a lower spring constant than in the first part region, or as a softer portion of the spring element.

FIG. 14 shows a side view of the spring element with the axis (23) which divides the spring element into a top half (9o) and a bottom half (9u). The top half (9o) and the bottom half (9u) of the spring element, in this case, provide a first part region and a second part region. With reference to the axis, the top half is developed differently to the bottom half. The spring element is consequently not structured symmetrically. The spring element has a first part region (9o) with a first characteristic at right angles with respect to the axis (23) and a second part region (9u) with a second characteristic at right angles with respect to the first part region and with respect to the axis (23). In the present case, elevated x-shaped structures which make the spring element relatively more rigid here than in the second part region (9u), can be seen in the first part region (9o). There are no stiffening elements or elevations to be seen in the second part region (9u), which is why the spring element bends downward toward the second part region (9u) when force is applied in the direction of the axis (23). This is utilized for the installation position of the spring element in the receiving element (2a, 10). The second part region (9u) is arranged in the receiving element such that it is able to be supported against the wall of the receiving element of the spring element. The first part region (9o) can consequently be developed so as to be accessible from outside and without guidance through the receiving element of the spring element. This provides advantages during cleaning of the PI.

If one also looks at the part regions (9h, 9i), the spring element has at least two part regions. In the present case, the spring element has at least four part regions (9h, 9i, 9o, 9u).

Figure 15A:
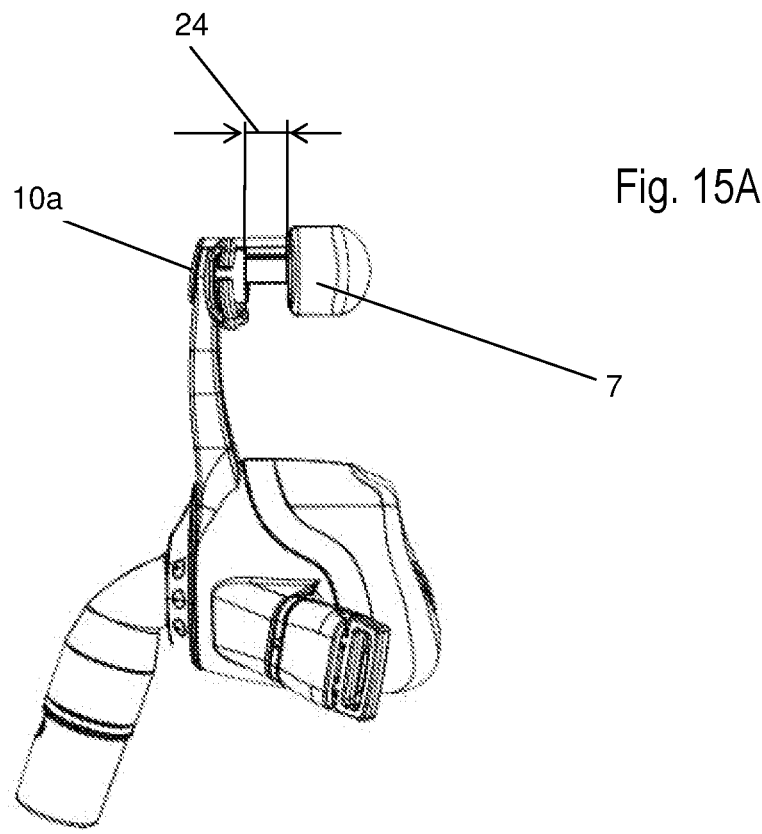
FIG. 15A and FIG. 15B: adjusting path and spring excursion of support body
Figure 15B:
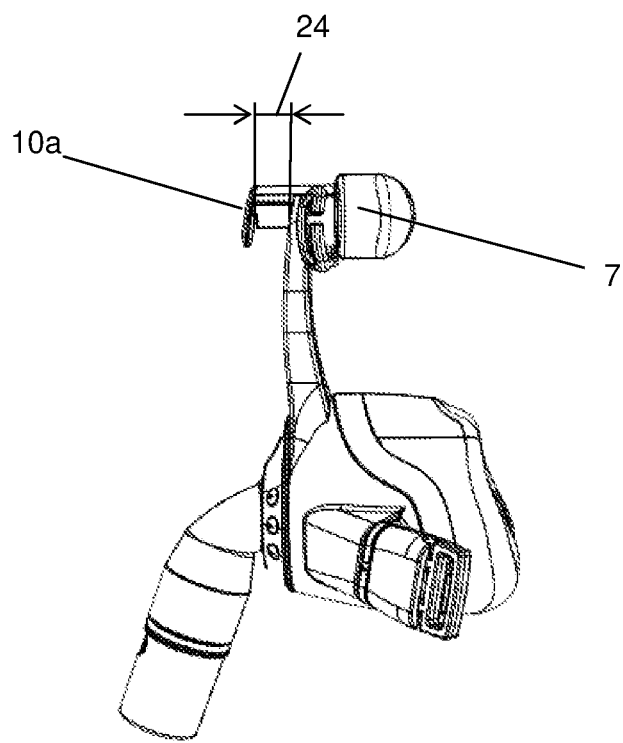

FIG. 15A and FIG. 15B show the adjusting path or spring excursion (24) of the support body (7) which is defined by the stop (10a).

The following can apply to all the embodiments of the invention:

The spring element which at right angles with respect to the axis (23) has a first part region (9h), in this case produced as a result of the relief cut as a square geometric recess, with a first characteristic, which is realized in this case as a higher spring constant or as a harder portion. A second part region (9i) is realized away from the location of the first part region, in this case as a result of the relief cut as a triangular geometric recess (with a rounded base), which has a second characteristic. The second characteristic, in this case, is realized as a lower spring constant than in the first part region, or as a softer portion of the spring element.

The first and second part regions of the spring element can also be located opposite one another, the first part region having a higher degree of rigidity or spring constant than the second part region.

A part region can have a higher degree of rigidity or spring constant as a result of geometric structures (such as, for example, ribbing, contour, open contour and closed contour).

A part region can have a higher degree of rigidity or spring constant as a result of different materials (for example different Shore hardnesses, within the range of Shore A 20-80, joined using a two-component method).

A part region can have a higher degree of rigidity or spring constant as a result of different wall thicknesses.

The following also can apply to all embodiments of the invention: The restoring force of the spring element (9, 9') and the restoring force of the forehead support pad (8) are designed such that, when the harness of the patient interface (1) is placed in position/tightened, the forehead support pad (8) first of all adapts to the shape of the face of the user or to the forehead of the user and only then with increasing tightening force of the harness is the spring element (9, 9') gradually compressed. By means of the tightening force of the harness, which the user adjusts himself and consequently determines, said user thus determines the position of the patient interface in relation to the forehead and consequently the inclination of the patient interface on the face. According to the present invention, it is also possible to design the restoring force of the spring element (9, 9') and the restoring force of the forehead support pad (8) to be approximately the same or to design the restoring force of the forehead support pad (8) such that the spring element is compressed first of all. According to the present invention, it is also provided that the spring element (8, 9, 9') is formed by the forehead support pad. According to the present invention, it is also provided that the spring element (8, 9, 9') has different spring characteristics.

To ensure this, in an advantageous manner no latching stages are provided. The particular advantage for the user is the stepless fine adjustment resulting from the automatic adjustment of the forehead supports. However, it is also possible to provide at least one latching stage which is, however, able to be overcome as a result of an additional application of force.

As a result of the equilibrium of forces between the tightening force of the head harness and the restoring force of the spring element of the forehead support, optimum and fault-free adaptation is ensured at all times, even if the patient changes his position when asleep.

It has been established in a surprising manner within the framework of the present invention that, in the case of a patient interface of the type according to the invention, a narrowly defined adjusting region, which corresponds substantially to the spring excursion, is sufficient for the support body to cover approximately 90% of patient faces. The spring excursion (24) of the spring element (8, 9, 9') consequently lies in the case of all the variants in the range of from 5 mm to 30 mm, 7 mm to 17 mm, in a preferred manner from 8 mm to 15 mm and in a particularly preferred manner from 9 mm to 14 mm. The spring excursion of the spring element (9, 9') can also be about 12 mm.

It has been established in a surprising manner within the framework of the present invention that, in the case of a patient interface of the type according to the present invention, a narrowly defined spring constant of the spring element is sufficient to provide precise fitting and pleasant support to approximately 90% of patients.

The spring constant of the spring element (8, 9, 9') is within the range of from 0.1 to 2.0 N/mm and in a preferred manner from 0.1 to 1.0 N/mm, or also from 0.1 to 0.5 N/mm; a range from 0.15 to 0.3 N/mm is also conceivable.

REFERENCE NUMERALS

1 Patient interface
2 Mask body
2*a* Receiving element of the support body
2*b* Receiving region for the spring
2*c* Connecting webs
2*d* Chamfers
3 Mask bead
4 Hose coupling
4*a* Rotary sleeve
5 Receiving device for the harness on the mask body
6 Harness receiving element—forehead support carrier
7 Support body
8 Forehead support pad
9 Spring element
9*a* Thickening, plate on spring element
9*b* Undercut on spring element
9*c* X-shaped spring structure
9*d* Relief cut
9*e* Struts between the X-forms
9*f* Centering element
9*g* Reinforcement of the X-shaped spring structure
9*h*, 9*i* Part regions of the spring element
9*o*, *u* Part regions of the spring element
9' Spring element, compression spring
10 Cylindrical guide/spring receiving means
10*a* Stop plate
11 Guide element
12 Lugs
12*a* Webs
13 Slots
14 Opening for the spring element
15 Abutment face for spring element in receiving element (2*a*)
16 Guide grooves
17 Receiving regions
18 Opening for spring element in receiving element (2*a*)
19 Abutment face for spring element in support body (7)
20 Harness
21 Velcro fastening
22 Harness ends
23 Axis
24 Spring excursion While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A spring element, wherein the spring element is suitable for use with a patient interface and in the form of an elongated body and has an axis along which the spring element is compressed, and wherein arranged in a direction of the axis, the spring element comprises a first region and a second region, at least one physical characteristic of the spring element in the first region having a value which is different from a value of the at least one physical characteristic in the second region, and wherein
   (i) the spring element has a spring element constant of from 0.1 to 2.0 N/mm; and/or (ii) the spring element provides a spring excursion over a range of from 5 mm to 30 mm; and/or (iii) the at least one physical characteristic is a degree of rigidity and the difference in the degree of rigidity is due to a difference in materials of the two regions; and/or (iv) the at least one physical characteristic is a spring element constant and the difference in the spring element constant is due to a difference in materials of the two regions; and/or (v) a characteristic curve of the spring element has multiple stages as a result of different elastomer materials used for producing the spring element; and/or (vi) a characteristic curve of the spring element has multiple stages as a result of a different geometries or geometric recesses inside the spring element.

2. The spring element of claim 1, wherein at least (i) applies.

3. The spring element of claim 1, wherein at least (ii) applies.

4. The spring element of claim 1, wherein at least (i) and (ii) apply.

5. The spring element of claim 1, wherein at least (iii) applies.

6. The spring element of claim 5, wherein the difference in the degree of rigidity is due to a difference in Shore A hardness of the materials within a range of from 20 to 80.

7. The spring element of claim 1, wherein at least (iv) applies.

8. The spring element of claim 7, wherein the difference in the spring element constant is due to a difference in Shore A hardness of the materials within a range of from 20 to 80.

9. The spring element of claim 1, wherein at least (v) applies.

10. The spring element of claim 1, wherein at least (vi) applies.

* * * * *